US011806420B2

(12) United States Patent
Kling et al.

(10) Patent No.: US 11,806,420 B2
(45) Date of Patent: Nov. 7, 2023

(54) COMPOSITIONS AND METHODS OF USE THEREOF FOR ANTISEPTIC MOUTH RINSES

(71) Applicant: Benova Rx LLC, Aubrey, TX (US)

(72) Inventors: William O. Kling, Aubrey, TX (US); Kendell Dean, Aubrey, TX (US)

(73) Assignee: Benova Rx LLC, Aubrey, TX (US)

(*) Notice: Subject to any disclaimer, the term of this patent is extended or adjusted under 35 U.S.C. 154(b) by 52 days.

(21) Appl. No.: 17/691,002

(22) Filed: Mar. 9, 2022

(65) Prior Publication Data
US 2022/0287945 A1 Sep. 15, 2022

Related U.S. Application Data

(60) Provisional application No. 63/159,802, filed on Mar. 11, 2021.

(51) Int. Cl.
*A61K 8/66* (2006.01)
*A61K 8/20* (2006.01)
*A61K 8/34* (2006.01)
*A61K 8/9789* (2017.01)
*A61Q 11/00* (2006.01)

(52) U.S. Cl.
CPC ............. *A61K 8/66* (2013.01); *A61K 8/20* (2013.01); *A61K 8/34* (2013.01); *A61K 8/9789* (2017.08); *A61Q 11/00* (2013.01)

(58) Field of Classification Search
None
See application file for complete search history.

(56) References Cited

U.S. PATENT DOCUMENTS

| | | |
|---|---|---|
| 2004/0166136 A1 | 8/2004 | Morelli et al. |
| 2010/0047190 A1 | 2/2010 | Reindl et al. |
| 2011/0081628 A1 | 4/2011 | Alden, IV et al. |
| 2013/0216596 A1 | 8/2013 | Viladot Petit et al. |
| 2014/0227202 A1 | 8/2014 | Pilgaonkar et al. |
| 2019/0343751 A1 | 11/2019 | Gontarz |

FOREIGN PATENT DOCUMENTS

GB 2289841 A 12/1995

*Primary Examiner* — Nannette Holloman
(74) *Attorney, Agent, or Firm* — Winstead PC

(57) ABSTRACT

In an embodiment, the present disclosure relates to a two-part oral rinse composition having a first rinse portion and a second rinse portion. In some embodiments, the first mouth rinse portion includes sodium chlorite ($NaClO_2$) in a first solution. In some embodiments, the second mouth rinse portion includes a sugar alcohol, a licorice root extract, and an enzyme in a second solution. In some embodiments, the enzyme can include, without limitation bromelain, actinidin, ficin, papain, and combinations thereof. In some embodiments, the first solution has a pH in a range of approximately 8.0 to approximately 12. In some embodiments, the second solution has a pH in a range of approximately 5.0 to approximately 6.5.

20 Claims, No Drawings

COMPOSITIONS AND METHODS OF USE THEREOF FOR ANTISEPTIC MOUTH RINSES

CROSS-REFERENCE TO RELATED APPLICATIONS

This patent application claims priority from, and incorporates by reference the entire disclosure of, U.S. Provisional Application 63/159,802 filed on Mar. 11, 2021.

TECHNICAL FIELD

The present disclosure relates generally to mouth rinses and more particularly, but not by way of limitation, to compositions and methods of use thereof for antiseptic mouth rinses.

BACKGROUND

This section provides background information to facilitate a better understanding of the various aspects of the disclosure. It should be understood that the statements in this section of this document are to be read in this light, and not as admissions of prior art.

Dental plaque and dental caries, the decay and crumbling of teeth, are among the most common diseases worldwide, and are caused by a mixture of microorganisms and food debris. More than 700 bacterial species have been found in the oral cavity; however, these bacteria are not all present in every mouth. The bacterial makeup varies in different sites in the oral cavity. For example, a large and more diverse bacterial load is often found on the dorsum of the tongue. Most of the microbes are harmless, but under certain conditions, some can cause oral infections, such as, but not limited to, caries (tooth decay) or periodontal disease (gum disease).

Moreover, various disease treatments, for example, cancer treatments, can cause mouth sores (oral mucositis). Cancer-related mouth sores generally form on the inside lining of the mouth or on the lips. The sores typically appear burn-like and can be painful, making it difficult to eat, talk, swallow, and even breathe. Sores can appear on any of the soft tissues of the lips or mouth, including the gums, tongue, and roof or floor of the mouth. Additionally, sores can also extend into the tube (esophagus) that carries food to the stomach. Current mouth rinses are generally abrasive, and thus, further irritate these sores, or prevent a user from cleaning their mouth in general. Thus, mouth rinses that reduce pain and inflammation of various types of mouth sores, for example treatment-induced, stress related, or bacteria-induced mouth sores, are needed.

Furthermore, the human oral cavity can experience many detrimental conditions, including, but not limited to, dental plaque and dental caries, periodontal disease, lichen planus, leukoplakia, oral candidiasis or oral thrush (*Candida albicans*), dry mouth which can often be caused by medications or diabetes, chemical or thermal burns, and combinations of the same and like.

One approach to decrease the chances of oral infection, in addition to daily brushing and flossing of teeth, is the use of oral mouth rinses. However, many mouth rinses are highly aggressive, and thus, more abrasive to tissue in the mouth. Abrasive mouth rinses cause irritation and can even harm gum tissue already irritated by oral infection. As such, a need exists for a gentle antiseptic mouth rinse that is both effective and gentle on tissue in the mouth and reduces pain and speeds healing. Various embodiments of the present disclosure seek to address the aforementioned need.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure relates to a two-part oral rinse composition having a first rinse portion and a second rinse portion. In some embodiments, the first mouth rinse portion includes sodium chlorite ($NaClO_2$) in a first solution. In some embodiments, the second mouth rinse portion includes a sugar alcohol, a licorice root extract, and an enzyme in a second solution. In some embodiments, the enzyme can include, without limitation bromelain, actinidin, ficin, papain, and combinations thereof. In some embodiments, the first solution has a pH in a range of approximately 8.0 to approximately 12. In some embodiments, the second solution has a pH in a range of approximately 5.0 to approximately 6.5.

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

*Streptococcus mutans* is a facultative anaerobic, gram-positive, coccus commonly found in the human oral cavity and is a significant contributor to dental plaque, and eventually, tooth decay. Three steps are involved in the formation of dental plaque. First, salivary molecules become attached to the enamel as soon as a tooth has been cleaned. As a consequence, the enamel is soon coated with a biofilm (pellicle), a slime-layer having millions of bacterial cells, salivary polymers, and food debris. Uncontrolled, this biofilm can easily reach a thickness of hundreds of cells on the surfaces of the teeth. The formed biofilm, also called plaque, provides an excellent adhesion site for the colonization and growth of many bacterial species.

Second, certain bacteria that are a part of the normal flora of the mouth have the ability to interact with, bond with, and colonize this biofilm. The biofilm formation of the primary colonizers, mainly *Streptococcus sanguis* and *Actinomyces viscosus*, is influenced by a number of environmental parameters, such as, but not limited to, bacteria concentration and pH. Under healthy conditions, these primary colonizers can modify the oral environment making it less hospitable for unfavorable bacteria.

Third, diets rich in sucrose allow for unfavorable bacterial species, such as, but not limited to, *S. mutans*, to adhere to the primary colonizers by cell-to-cell interactions. Subsequent bacterial growth on the tooth surface leads to additional formation of biofilm on the teeth, also referred to as dental plaque. A continued increase in dietary carbohydrates, which is primarily sucrose, results in further growth of unfavorable bacteria and biofilm. A diet containing sucrose is one of the main reasons for the high dental caries rate in developed countries.

Saliva, with a pH of about 6.7, can neutralize the low pH generated by *S. mutans* and help remove dental plaque. However, acid production fueled by sucrose, or other sugars, can overwhelm the capacity of the saliva to remove acid end products and the neutralizing power of the salivary and plaque buffer system.

*S. mutans* gives its name to a group of seven closely related species, collectively referred to as the mutans streptococci. The primary habitats for *S. mutans* are the mouth, the pharynx, and the intestine. Several factors are present in dental caries, such as, but not limited to, adherence to enamel surfaces, production of acidic metabolites, capacity to build up glycogen reserves, and an ability to synthesize extracellular polysaccharides (EPS). *S. mutans* and *S. sobrinus* play a role in the cause of dental caries, as these bacteria can adhere to the thin film coating on the enamel (pellicle) by bonding with plaque bacteria commonly found in the mouth (*Streptococcus sanguis* and *Actinomyces viscosus*). Mutans streptococci and *lactobacilli*, another cavity-causing bacterium, are both strong acid producers, and hence, cause an acidic environment which creates an increased risk for cavities.

Usually, the appearance of *S. mutans* in the tooth cavities is followed by caries after approximately 6 to 24 months. The acid-generating *S. mutans* and *S. sobrinus* are able to form extracellular polysaccharides in the presence of sucrose, but also from fructose and glucose. The EPS are long-chained and high molecular mass polymers on an external surface of the bacteria that create biofilm scaffolding and ensure bacteria are able to anchor themselves in the dental plaque. The energy-rich glycosidic bond between the glucose and fructose moieties supplies the free energy needed for the synthesis of EPS. The production of large quantities of EPSs from sucrose is a factor of *S. mutans* cariogenicity.

Any carbohydrate that dental plaque bacteria can utilize as an energy source contributes to the virulence of the microorganisms at a given site, and thus, has a cariogenic potential. Sucrose is not only rapidly fermented to acidic end products, but it is also a dietary carbohydrate that can be transformed into EPS in the plaque. Thus, it is considered to be the most cariogenic carbohydrate in the human diet. EPSs effect the progress of dental caries by: (1) providing a reserve of substrates via polysaccharides; (2) providing scaffolding that aids adherence of bacteria; (3) trapping acid near the tooth surface via water-insoluble EPSs acting as diffusion barriers; and (4) increasing plaque thickness, and thus, increasing acid retention time. The role of glucans and fructans in the diffusion of ions through cell concentrates has been studied. It was concluded that water-insoluble glucans provide a source of fermentable substrates. Thus, it has been suggested that water-insoluble glucans can enhance the cariogenic potential of EPSs by allowing for greater and more sustainable access to nutrients. Glucans act as adhesives on teeth surfaces, and therefore aid the cariogenicity of *S. mutans*. In addition, glucans aid in cell-to-cell and cell-to-surface adhesive interactions in plaque with dextran-mediating bacterial aggregation. Studies have indicated that the main role of EPSs in cariogenicity of *S. mutans* is due to its adherence properties.

The control of plaque can be achieved by mechanical oral hygiene procedures, such as, for example, daily brushing of the teeth, but in many cases, this is not enough. Thus, addition of antiplaque, antibacterial, or antimicrobial agents to dental health care products has been advantageous. Mechanisms by which plaque can be controlled by use of antiplaque, antibacterial, or antimicrobial agents include, but are not limited to, reducing the overall rate of accumulation of new plaque, reducing or removing existing plaque, inhibiting only the growth of those species implicated in a disease, inhibiting the production of EPSs, and combinations of the same and like.

Additionally, mouth sores are common ailments that affect many people at some point in their lives. These sores can appear on any of the soft tissues of the mouth, including the lips, cheeks, gums, tongue, and the floor and roof of the mouth. Some sores even develop and/or spread to the esophagus. Mouth sores (including canker sores) are usually a minor irritation and last only a week or two. However, in some cases, they can indicate mouth cancer or an infection from a virus, such as herpes simplex, or be the result of various types of disease treatments (e.g., cancer treatments). In most cases, mouth sores cause some redness and pain, especially when eating and drinking. They can also cause a burning or tingling sensation around the sore. Depending on the size, severity, and location of the mouth sores, they can make it difficult to eat, drink, swallow, talk, or breathe. These conditions make it difficult to keep the mouth clean, as most mouth rinses are harsh on the soft tissue in the mouth. The pain caused while cleaning discourages users from continuing activities, such as cleaning their mouths. Accordingly, gentle mouth rinses that can also reduce inflammation and pain associated with mouth sores and speed healing are highly desired.

Various compositions are effective at preventing various oral conditions, such as, for example, dental plaque and dental caries, periodontal disease, lichen planus, leukoplakia, oral candidiasis or oral thrush, dry mouth, chemical or thermal burns, mouth sores, and combinations of the same and like. For example, sodium chlorite ($NaClO_2$) has been shown to kill bacteria, yeast, mold, and viruses in the oral cavity. $NaClO_2$ is naturally "activated" by the acidic pH of saliva and the acidic surface or mantel of *S. mutans* and other detrimental organisms in the mouth. When $NaClO_2$ comes into contact with an acid, or otherwise acidic substance, the pH of composition drops, the sodium chlorite converts to chlorine dioxide ($ClO_2$), and becomes much more active.

Saliva is somewhat acidic, having a pH of approximately 6.70. However, the strong activity of $NaClO_2$ occurs when the solution having $NaClO_2$ comes in contact with *S. sobrinus*, *S. mutans*, and other detrimental organisms with a low pH. Typically, the healthy skin cells in the oral cavity have stronger cell membranes compared to bacteria and dead skin cells. As such, the $ClO_2$ generally reacts with bacteria in the mouth or dead skin cells before healthy skin cells. This results in killing the bacteria and cleaning the oral cavity. The activation of $NaClO_2$ kills bacteria, yeast, mold, fungus, and viruses, and can also eliminate bad breath. Bad breath comes from numerous conditions, including poor dental hygiene, tobacco use, certain foods, having a dry mouth, various medications, infections in the mouth, and combinations of the same and like. The activation of $NaClO_2$ into $ClO_2$ results in the breakdown of food particles, killing bacteria, yeast, mold, and fungus, and removal of dead oral tissue, all of which can cause bad breath.

However, $NaClO_2$ rinses, depending on the makeup of the formulation, can be harsh on tissue in the oral cavity. As such, the present disclosure seeks to remedy this deficiency of $NaClO_2$ based formulations. One aspect of the present disclosure is directed to optimizing the use of $NaClO_2$ based mouth rinses to not make them too strong for prolonged use for oral hygiene. NaClO$_2$ concentration can easily be increased to kill virtually all bacteria and fungi in less than 10 seconds with a greater than 99% kill rate. However, this will also leave excess ClO$_2$ in the oral cavity, with activity continuing until all the ClO$_2$ is used up. Thus, if the detrimental organisms, dead tissue cells, and food particles have been consumed, the excess ClO$_2$ will break down healthy tissue, leading to oral irritation.

Xylitol is a sugar alcohol or polyol that is naturally present in the human metabolism, and can thus be safely used in dental products or as a food ingredient. It has been shown that xylitol has antimicrobial properties and that systematic use of xylitol reduces the incidence of caries and growth of *S. mutans*. Additionally, xylitol has been reported to affect the synthesis of polysaccharides in *S. mutans*, which leads to a decreased bacterial adherence. Moreover, xylitol is non-cariogenic since *S. mutans* is not able to ferment xylitol.

Contrastingly, triclosan, an organic compound with antibacterial properties, has historically been used in toothpaste for decades, and has been shown to have an inhibitory effect on bacterial metabolism in dental plaque and to improve gingival health. Triclosan inhibits the growth of *S. mutans* by sensitizing glycolysis to acid inhibition by acting with weak-acid transmembrane proton carriers, such as fluoride. However, xylitol can be considered as a safer substance to use than triclosan for the prevention of plaque, since triclosan can react with chlorine in tap water and form chloroform, and is hence considered to be toxic. In addition, xylitol has received an anti-cariogenic claim approval by the European Food Safety Authority.

Xylitol has been demonstrated to provide anti-adhesion properties by acting as a biofilm disperser against *S. mutans* and *Candida* spp. Xylitol has been shown to inhibit bacteria and yeast adhesion in the oral cavity. Without being bound by theory, it is believed that xylitol provides these benefits by a blockage of lectin-like receptors, an elevation of osmotic pressure, an inhibition of the phosphoenolpyruvate-phosphotransferase system, and modification of gene expression.

Additionally, xylitol exhibits cytotoxic behavior against mutans streptococci, and furthermore inhibits the growth of mutans streptococci by disrupting their energy production process, leading to cell death. *S. mutans* transports xylitol into the cell in an energy-consuming cycle that is responsible for growth inhibition. Xylitol is then converted to xylitol-5-phosphate via phosphoenolpyruvate (fructose phosphotransferase system by *S. mutans* resulting in development of intracellular vacuoles and cell membrane degradation). Contributing to its own death, *S. mutans* then dephosphorylates xylitol-5-phosphate. The dephosphorylated molecule is then expelled from the cell, and this expulsion occurs at an energy cost with no energy gained from xylitol metabolism. Cell death occurs when dephosphorylated xylitol-5-phosphate is expelled from the cell at an energy cost that the cell cannot afford. Thus, xylitol improves cariostatic effects in the oral cavity.

Saliva protects oral mucosa and teeth against harmful substances and lubricates the mouth to facilitate chewing, swallowing, and speech. Saliva also reduces tissue trauma. Saliva is an exocrine secretion where the various constituents act alone or in in combination with other constituents to perform different functions in the oral cavity. For example, saliva buffers acid, helps prevent gingival mucosal erosions, and aids in tooth remineralization. However, when salivary functions are diminished, there is a greater risk of developing caries, experiencing denture discomfort, and having diseases, such as, for example, candidiasis. Studies indicate that xylitol increases salivary flow which promotes remineralization due to increased flow of saliva rich in calcium and phosphate. Additionally, xylitol has been shown to increase the pH in the mouth and reduce plaque levels. Accordingly, xylitol can provide for an advantageous compound in the promotion of good oral hygiene and its use in various oral hygiene formulations can be highly effective at preventing various oral conditions, such as, for example, dental plaque and dental caries, periodontal disease, lichen planus, leukoplakia, oral candidiasis or oral thrush, dry mouth, chemical or thermal burns, and combinations of the same and like.

In addition to xylitol, licorice root extract has been shown to be advantageous for use in oral hygiene as well. Licorice root extract is obtained from perennial plants native to Mediterranean countries, central to southern Russia, and certain regions of Asia. *Glycyrrhiza glabra* and *Glycyrrhiza uralensis* are the most common sources of licorice root extracts for use in cosmetics, foods, tobacco, and in traditional and herbal medicine.

*Glycyrrhiza glabra* has been shown to coat the surfaces of teeth, provide anti-adherent properties against *S. mutans* and *C. albicans*, reduce alveolar bone loss, reduce growth of *C. albicans*, and cause a stimulatory effect on bone formation. Glycyrrhizin, the main triterpenoid saponin glycoside in *G. glabra*, in the presence of sucrose almost completely inhibits the ability of sucrose to adhere to a surface, which indicates an anti-adherent property of glycyrrhizin. Further investigations showed that glycyrrhizin dose-dependently inhibits the glucosyltransferase activity of *S. mutans*, which is involved in the formation of insoluble glucans required for biofilm formation in the oral cavity. Additionally, it has been identified that *G. glabra* provides this anti-adherent property to both *S. mutans* and *C. albicans*, and reduces the grown of *C. albicans*.

Moreover, studies indicate that glabridin, a chemical found in the root extract of *G. glabra*, can interfere with osteoclastic cell maturation and functions, thus giving *G. glabra* potential for therapeutic application in the treatment and prevention of bone loss related to inflammatory disorders, such as, for example, periodontal disease. In fact, studies indicate that glabridin has a direct stimulatory effect on bone formation by enhancing the proliferation of osteoblasts as well as the ability to synthesize collagen. These studies indicate that *G. glabra* not only reduces alveolar bone loss, but also further stimulates the effect of bone formation.

In addition to *G. glabra*, *G. uralensis* also has various advantageous properties for promotion of oral hygiene and prevention of adverse oral conditions. For example, *G. uralensis* has been shown to inhibit growth and biofilm formation of *P. gingivalis*, inhibit the growth of *S. mutans*, provide anti-inflammatory properties when used long term, and provide anti-adherent properties against *C. albicans*. As such, the licorice root extract *G. glabra* and *G. uralensis* can also provide for an advantageous compound in the promotion of oral hygiene and its use in various formulations can be highly effective at preventing various oral conditions, and reducing inflammation of, for example, mouth sores. Other, licorice extracts are also envisioned and include, without limitation, *Glycyrrhiza glabra*, *Glycyrrhiza inflata*, and *Glycyrrhiza uralensis* extracts.

Bromelain has been shown to exhibit anti-inflammatory properties. Bromelain is a complex natural mixture of proteolytic enzymes derived from pineapple (*Ananas cosmosus*) and possesses many notable therapeutic properties.

Studies have demonstrated that suppression of chronic inflammation may reduce the cancer incidence and also inhibit cancer progression. Cyclooxigenase-2 (COX-2) is a component of cancer-associated inflammation that is involved in the synthesis of prostaglandin E2 (PGE-2). PGE-2 is a pro-inflammatory lipid that also acts as an immunosuppressant. COX-2 converts arachidonic acid into PGE-2 and promotes tumor angiogenesis and cancer progression. Studies show that bromelain downregulates COX-2 and PGE-2 expression levels in murine microglial cells and human monocytic leukemia cell lines. Bromelain activates the inflammatory mediators, including interleukin (IL)-1β, IL-6, interferon (INF)-γ, and tumor necrosis factor (TNF)-α in mouse macrophage and human peripheral blood mononuclear cells (PBMC). These results indicated that bromelain potentially activates the healthy immune system in association with the rapid response to cellular stress. Conversely, bromelain reduces IL-1β, IL-6, and TNF-α secretion when immune cells are already stimulated in the condition of inflammation-induced over production of cytokines.

Moreover, studies show that bromelain reduced the expression of INF-γ and TNF-α in inflammatory bowel disease. One study demonstrated that bromelain diminished the cell damaging effect of advanced glycation end products by proteolytic degradation of receptor of advanced glycation end products and controlled the inflammation. The cell surface marker, cluster of differentiation (CD) is expressed by cancer and immune cells directly involved in cancer growth and metastasis. Additionally, CD44 regulates lymphocyte requirement at the site of inflammation. Bromelain reduces the level of CD44 expression on the surface of mouse and human tumor cells, and regulates lymphocyte homing and migration to the sites of inflammation. Furthermore, bromelain modulates the expression of transforming growth factor (TGF)-β, one of the major regulators of inflammation in patients affected by osteomyelofibrosis and rheumatoid arthritis. In addition, various studies report the immunomodulatory effect of bromelain. Bromelain activates natural killer cells and augments the production of granulocyte-macrophage-colony stimulating factor, IL-2, IL-6, and decreases the activation of T-helper cells.

These findings indicate that bromelain decreases the majority of inflammatory mediators and demonstrates a role as an anti-inflammatory agent. Furthermore, these findings indicate that bromelain reduces TNF-α, a major driver of inflammation and pain. These studies indicate that bromelain exhibits anti-inflammatory, and thus, analgesic properties, making bromelain an effective component for treatment of inflammation and pain caused by inflammation or soft-tissues swelling (e.g., sores in the mouth). Furthermore, bromelain, when included in mouth rinses, show fast-acting and quick relief from pain and/or inflammation caused by mouth sores. This can prove highly advantageous when used in mouth rinses to provide cleaning of the mouth sores while also providing fast pain relief and healing. As discussed above, bromelain has several advantages. In addition to bromelain, other various enzymes can be utilized. For example, aside from bromelain, the enzyme can include, without limitation, actinidin, ficin, papain, and combinations thereof. Though examples shown below utilize bromelain as the enzyme, other enzymes, such as actinidin, ficin, and papain are readily envisioned, and can be used in combination with bromelain, or as an alternative to bromelain.

In view of the aforementioned properties of $NaClO_2$, xylitol, licorice root extracts, and bromelain, an embodiment of the present disclosure is directed to oral mouth rinses that can kill and prevent the regrowth of oral bacteria, yeast, and mold. Additionally, the mouth rinses of the present disclosure increase salivary flow to thereby relieve dry mouth and promote remineralization of teeth. Moreover, the mouth rinses of the present disclosure further provides for pH regulation by increasing the pH to a beneficial level of, for example, a pH of 5.8. Furthermore, the mouth rinses of the present disclosure further provide for anti-inflammatory properties which can promote healing and pain relief from a user suffering from an oral infection or mouth sores. In addition, the mouth rinses of the present disclosure can further include galactoarabinan. Glactoarabinan is a natural polysaccharide that reduces trans-epidermal water loss, retaining moisture and preventing or resolving dry mouth. In addition, it has demonstrated the ability to allow ingredients to adhere to the oral cavity (e.g., leaving a coating on the soft tissue in the oral cavity) for a longer period of time, thus allowing for prolonged cleaning and healing in the mouth. In various embodiments, the mouth rinses can include various thickening agents, for example, guar, xanthan, and combinations thereof.

In a typical embodiment, the mouth rinses of the present disclosure can include two mouth rinses to maximize the efficacy of $NaClO_2$, xylitol, licorice root extract, and bromelain. Each mouth rinse, when used in combination, provide for a synergistic effect, thus increasing efficacy of each mouth rinse when used together. While in some embodiments, each mouth rinse can be used independently, bacteria kill rates and other benefits show stronger results when used in combination with each other. The mouth rinses of the present disclosure generally relate to $NaClO_2$ based mouth rinses and mouth rinses having xylitol, licorice root extract, and bromelain. However, in some embodiments, the present disclosure relates to a $NaClO_2$ mouth rinse and a mouth rinse including at least one of xylitol, licorice root extract, or bromelain. In various embodiments, the mouth rinses of the present disclosure can include a mouth rinse having xylitol. In some embodiments, the mouth rinses of the present disclosure can include a mouth rinse having licorice root extract. In some embodiments, the mouth rinses of the present disclosure can include a mouth rinse having bromelain. Disclosed herein are compositions and methods relating to a gentle $NaClO_2$ mouth rinse showing high efficacy when used in combination with xylitol, licorice root extract, and/or bromelain based mouth rinses.

Working Examples

Reference will now be made to more specific embodiments of the present disclosure and data that provides support for such embodiments. However, it should be noted that the disclosure below is for illustrative purposes only and is not intended to limit the scope of the claimed subject matter in any way.

In a typical embodiment, the mouth rinses of the present disclosure relate to two separate mouth rinses, a $NaClO_2$ based mouth rinse and a xylitol, licorice root extract, and bromelain based mouth rinse. The first mouth rinse, discussed in further detail below, includes the use of $NaClO_2$ and its activation into $ClO_2$. In some embodiments, the $NaClO_2$ based mouth rinse is rinsed around inside the mouth for approximately 45 seconds, primarily killing bacteria, and secondarily killing fungi and other detrimental or unwanted organisms. In some embodiments, the $NaClO_2$ based mouth rinse is shelf-stable at a pH of approximately 8.40. In some embodiments, the $NaClO_2$ mouth rinse is shelf-stable at a pH in a range of approximate 8.0 to 9.5. The $NaClO_2$ based mouth rinse is lightly buffered so interaction with any acid, or acidic fluid or organism, will significantly lower the pH of the mouth rinse.

As discussed above, when the $NaClO_2$ comes into contact with an acid or otherwise acidic constituent or surface, and the pH of the mouth rinse drops, the $NaClO_2$ converts to $ClO_2$ and becomes more active. In some embodiments, the pH of the $NaClO_2$ based mouth rinse is decreased by the acidity of saliva and various organisms in the oral cavity, such as, for example, *S. sobrinus* and *S. mutans*. This activation promotes the killing of bacteria and fungi in the oral cavity.

One consideration in optimizing the formulation of the $NaClO_2$ based mouth rinse for continued non-abrasive use is to slightly weaken it. In this fashion, an approach is to maintain an optimal pH range. In some embodiments, the pH can be approximately 8.40, though in some embodiments the pH can range between about 8.0 to about 9.5. In some embodiments, the pH is below 10. In some embodiments, the pH is below 11. In some embodiments, the pH is below 12. Table 1, shown below, illustrates an embodiment of the present disclosure directed towards a $NaClO_2$ based mouth rinse.

TABLE 1

| Ingredient | Amount |
|---|---|
| Purified Water | 98.8300% |
| Sodium Chlorite | 0.1600% |
| Sodium Bicarbonate | 1.0000% |
| Citric Acid | 0.0070% |
| Disodium Phosphate | 0.0016% |
| Total | 100.0000% |
| pH | 8.40 |

A high increase of $NaClO_2$ can likely leave excess $ClO_2$ in the oral cavity, as discussed above, with activity continuing until the $ClO_2$ is used up. If the unwanted bacteria and fungi and dead tissue cells have been consumed, the excess $ClO_2$ will break down healthy tissue, leading to irritation, which is common in currently available $NaClO_2$ based mouth rinses. The formulation shown above in Table 1, and other embodiments discussed below, provides for a less abrasive rinse, and when used in combination with xylitol, licorice root extract, and bromelain mouth rinses, it does not compromise efficacy.

In some embodiments, each constituent of the mouth rinse formulation of Table 1 can have varying concentrations. For example, in some embodiments, the purified water can be in a range of about 85.0000 to about 99.0000% by total volume of the mouth rinse. In some embodiments, the sodium chlorite can be in a range of about 0.0500 to about 1.0000% by total volume of the mouth rinse. In some embodiments, the sodium bicarbonate can be in a range of about 0.0500 to about 2.0000% by total volume of the mouth rinse. In some embodiments, the citric acid can be in a range of about 0.0001 to about 1.0000% by total volume of the mouth rinse. In some embodiments, the disodium phosphate can be in a range of about 0.0001 to about 1.0000% by total volume of the mouth rinse.

In some embodiments, the $NaClO_2$ based mouth rinse of the present disclosure can further include disodium ethylenediaminetetraacetic acid (EDTA). In some embodiments, the disodium EDTA can be in a range of about 0.001 to 0.300% by total volume of the mouth rinse. In some embodiments, the disodium EDTA can be present in an amount of approximately 0.05% by total volume of the mouth rinse. In some embodiments, the $NaClO_2$ based mouth rinse of the present disclosure can further include at least one of sodium hydroxide or sodium carbonate as optional pH adjusters. In some embodiments, the $NaClO_2$ based mouth rinse of the present disclosure can further include potassium hydroxide. In some embodiments, the potassium hydroxide can be in a range of about 0.0001 to about 1.0000% by total volume of the mouth rinse. In such embodiments, the purified water can be adjusted to compensate for the overall volume.

Table 2, shown below, illustrates a kill rate test of a $NaClO_2$ based mouth rinse having a formulation as shown in Table 1 above. As illustrated in Table 2, the formulation from Table 1 has a less aggressive kill rate at 45 seconds, than that of currently available $NaClO_2$ based mouth rinses that are aggressive, as shown and discussed in further detail below. However, this can be beneficial when used in conjunction with xylitol, licorice root extract, and bromelain based mouth rinses. In some instances, the combination of the $NaClO_2$ and xylitol, licorice root extract, and bromelain based mouth rinses can be conducted at least twice a day. In some embodiments, the rinses can be conducted one or more times a day. In addition, Table 2 illustrates kill rates for the human coronavirus, indicating the potential to kill the human coronavirus and prevent possible infection and/or spreading of the virus.

TABLE 2

Kill Rate Test Results for Table 1 Formulation

| Organisms | | Log Reduction | Percent Reduction |
|---|---|---|---|
| *S. mutans* | 30 seconds | 2.37 | 99.57% |
| *S. mutans* | 45 seconds | 3.85 | 99.99% |
| *E. coli* | 30 seconds | 5.80 | 99.99% |
| *E. coli* | 45 seconds | 5.80 | 99.99% |
| *C. albicans* | 30 seconds | 1.21 | 93.82% |
| *C. albicans* | 45 seconds | 2.30 | 99.48% |
| Human Coronavirus | 30 seconds | 0.44% | 63.69% |
| Human Coronavirus | 45 seconds | 0.63% | 76.56% |
| Human Coronavirus | 90 seconds | 0.19% | 35.43% |

Table 3, shown below, illustrates an additional embodiment of the present disclosure directed towards a $NaClO_2$ based mouth rinse having another formulation.

TABLE 3

| Ingredient | Amount |
|---|---|
| Purified Water | 98.7965% |
| Sodium Chlorite | 0.1950% |
| Sodium Bicarbonate | 1.0000% |
| Citric Acid | 0.0070% |
| Disodium Phosphate | 0.0015% |
| Total | 100.00% |
| pH | 8.28 |

In some embodiments, each constituent of the mouth rinse formulation of Table 3 can have varying concentrations. For example, in some embodiments, the purified water can be in a range of about 85.0000 to about 99.0000% by total volume of the mouth rinse. In some embodiments, the sodium chlorite can be in a range of about 0.0500 to about 1.0000% by total volume of the mouth rinse. In some embodiments, the sodium bicarbonate can be in a range of about 0.0500 to about 2.0000% by total volume of the mouth rinse. In some embodiments, the citric acid can be in a range of about 0.0001 to about 1.0000% by total volume of the mouth rinse.

In some embodiments, the disodium phosphate can be in a range of about 0.0001 to about 1.0000% by total volume of the mouth rinse.

In some embodiments, the NaClO$_2$ based mouth rinse of the present disclosure can further include EDTA. In some embodiments, the disodium EDTA can be in a range of about 0.001 to 0.300% by total volume of the mouth rinse. In some embodiments, the disodium EDTA can be present in an amount of approximately 0.05% by total volume of the mouth rinse. In some embodiments, the NaClO$_2$ based mouth rinse of the present disclosure can further include at least one of sodium hydroxide or sodium carbonate as optional pH adjusters. In some embodiments, the NaClO$_2$ based mouth rinse of the present disclosure can further include potassium hydroxide. In some embodiments, the potassium hydroxide can be in a range of about 0.0001 to about 1.0000% by total volume of the mouth rinse. In such embodiments, the purified water can be adjusted to compensate for the overall volume.

Table 4, shown below, illustrates a kill rate test of a NaClO$_2$ based mouth rinse having a formulation as shown in Table 3 above.

TABLE 4

Kill Rate Test Results for Table 3 Formulation

| Organisms | | Log Reduction | Percent Reduction |
|---|---|---|---|
| S. mutans | 45 seconds | 5.69 | 99.99% |
| S. mutans | 1 minute | 5.69 | 99.99% |
| S. sanguinis | 45 seconds | 5.41 | 99.99% |
| S. sanguinis | 1 minute | 5.41 | 99.99% |
| E. coli | 45 seconds | 5.88 | 99.99% |
| E. coli | 1 minute | 5.88 | 99.99% |
| C. albicans | 1 minute | 5.75 | 99.99% |
| C. albicans | 3 minutes | 5.75 | 99.99% |

Table 5, shown below, illustrates a further embodiment of the present disclosure directed towards a NaClO$_2$ based mouth rinse having an alternative formulation.

TABLE 5

| Ingredient | Amount |
|---|---|
| Purified Water | 98.8214% |
| Sodium Chlorite | 0.1700% |
| Sodium Bicarbonate | 1.0000% |
| Citric Acid | 0.0070% |
| Disodium Phosphate | 0.0016% |
| Total | 100.00% |
| pH | 8.36 |

In some embodiments, each constituent of the mouth rinse formulation of Table 5 can have varying concentrations. For example, in some embodiments, the purified water can be in a range of about 85.0000 to about 99.0000% by total volume of the mouth rinse. In some embodiments, the sodium chlorite can be in a range of about 0.0500 to about 1.0000% by total volume of the mouth rinse. In some embodiments, the sodium bicarbonate can be in a range of about 0.0500 to about 2.0000% by total volume of the mouth rinse. In some embodiments, the citric acid can be in a range of about 0.0001 to about 1.0000% by total volume of the mouth rinse. In some embodiments, the disodium phosphate can be in a range of about 0.0001 to about 1.0000% by total volume of the mouth rinse.

In some embodiments, the NaClO$_2$ based mouth rinse of the present disclosure can further include EDTA. In some embodiments, the disodium EDTA can be in a range of about 0.001 to 0.300% by total volume of the mouth rinse. In some embodiments, the disodium EDTA can be present in an amount of approximately 0.05% by total volume of the mouth rinse. In some embodiments, the NaClO$_2$ based mouth rinse of the present disclosure can further include at least one of sodium hydroxide or sodium carbonate as optional pH adjusters. In some embodiments, the NaClO$_2$ based mouth rinse of the present disclosure can further include potassium hydroxide. In some embodiments, the potassium hydroxide can be in a range of about 0.0001 to about 1.0000% by total volume of the mouth rinse. In such embodiments, the purified water can be adjusted to compensate for the overall volume.

Table 6, shown below, illustrates a kill rate test of a NaClO$_2$ based mouth rinse having a formulation as shown in Table 5 above.

TABLE 6

Kill Rate Test Results for Table 5 Formulation

| Organisms | | Log Reduction | Percent Reduction |
|---|---|---|---|
| S. mutans | 45 seconds | 5.69 | 99.99% |
| S. mutans | 1 minute | 5.69 | 99.99% |
| C. albicans | 45 seconds | 4.45 | 99.99% |
| C. albicans | 1 minute | 5.75 | 99.99% |

The data shown above illustrates the antimicrobial power of the NaClO$_2$ based mouth rinses of the present disclosure. For the kill rate tests shown above, bacteria and fungi were picked based on their commonality found in the oral cavity, and are also major causes of cavities. Similar results are expected on other bacteria and fungi. The variables that effect the kill rate results in the oral cavity is the concentration of NaClO$_2$, the time the mouth rinse stays in the mouth, the pH of saliva in the mouth, and how fragile the pH is of the solution, that is, the easier it is for the pH of the solution to drop to the saliva pH, the faster and more effective the mouth rinse. Though, to a lesser degree, temperature can also make a difference with warmer temperatures being better for activity. However, the oral temperature in most users remains relatively constant throughout.

Table 7, shown below, illustrates two examples of currently available NaClO$_2$ based mouth rinses. As shown in Table 7 below, both Example 1 and Example 2 formulations exhibit high killing rates at 10 seconds. This, however, can easily cause irritation to tissue in the oral cavity and potentially worsen conditions in the oral cavity as these mouth rinses tend to be aggressive.

TABLE 7

Abrasive NaClO$_2$ Based Mouth Rinse

Kill Rate Test Results Example 1

| Organisms | | Log Reduction | Percent Reduction |
|---|---|---|---|
| S. mutans | 10 seconds | 5.69 | 99.99% |
| S. mutans | 45 seconds | 5.69 | 99.99% |
| C. albicans | 10 seconds | 5.75 | 99.99% |
| C. albicans | 45 seconds | 5.75 | 99.99% |

Kill Rate Test Results Example 2

| Organisms | | Log Reduction | Percent Reduction |
|---|---|---|---|
| S. mutans | 10 seconds | 4.00 | 99.99% |
| S. mutans | 45 seconds | 4.15 | 99.99% |
| C. albicans | 10 seconds | 4.12 | 99.99% |
| C. albicans | 45 seconds | 5.60 | 99.99% |

The NaClO$_2$ based mouth rinses disclosed herein provide for a gentler mouth rinse as compared to currently available products, such as Example 1 and Example 2 of Table 7. This is particularly important if the user has compromised tissue or inflammation in the mouth. A more aggressive product, such as those currently available, could easily cause irritation or make conditions in the oral cavity worse. Furthermore, the less abrasive nature of the NaClO$_2$ based mouth rinse disclosed herein also allows to be kept in the mouth for a longer period of time, resulting in a more even coverage and thorough cleansing, and continued killing of detrimental organisms.

Because the NaClO$_2$ based mouth rinse of the present disclosure is gentler compared to competitive rinses with higher NaClO$_2$ levels, more users will be able to keep the NaClO$_2$ based mouth rinse of the present disclosure in their mouth longer with no irritation. In a typical embodiment, rinse times can be approximately 45 seconds. This will allow the NaClO$_2$ to kill more bacteria than if used for only 30 seconds; however, in some embodiments, rinse times can be 30 seconds to provide for an even less abrasive treatment. In some embodiments, the rinse time can be greater than 45 seconds. For example, in some embodiments, the rinse time can be 1 minute. In contrast, currently available NaClO$_2$ mouth rinses have a 99% or more kill rate in 10 seconds for both S. mutans and C. albicans, as shown in Example 1 and Example 2 of Table 7, illustrating the aggressiveness the mouth rinses currently available.

Sodium bicarbonate is utilized in the formulations illustrated above, as it is easy to control raising the pH in comparison to, for example, potassium hydroxide. However, potassium hydroxide, or other pH buffering compounds are also envisioned so long as to keep the pH of the NaClO$_2$ based mouth rinse in a desired pH range. In a typical embodiment, a pH lower than 10 for the NaClO$_2$ based mouth rinse is desired. In some embodiments, the pH can be lower than 11. In some embodiments, the pH can be lower than 12. The pH of sodium bicarbonate in water is about 8.32, adding minimal amounts of disodium phosphate allow for the adjustment of the pH up from 8.32 to 8.47. In some embodiments, the pH is about 8.47 to stabilize the NaClO$_2$. In some embodiments, the pH is in a range from about 8.0 to about 9.5. However, the least amount of buffering possible is desirable in some embodiments so the pH will drop significantly when the NaClO$_2$ based mouth rinse encounters anything acidic in the oral cavity.

As such, other pH buffers are readily envisioned. For example, in some embodiments, the pH buffers can include, without limitation, sodium hydroxide, calcium hydroxide, potassium hydroxide, borate-type buffering agents, N-cyclohexyl-2-aminoethanesulfonic acid (CHES), monosodium phosphate, calcium carbonate, sodium bicarbonate, disodium phosphate, bicarbonate buffering systems, phosphate buffering systems, alkaline buffering systems, acetate buffering systems, citric acid, and combinations thereof. In some embodiments, NaClO$_2$ can be substituted with any other antimicrobial agents such as, for example, sodium hypochlorite, sodium chlorate, or potassium chlorate. In some embodiments, NaClO$_2$ can be substituted for a chlorous acid (HClO$_2$) solution. As such, other antimicrobial agents are readily envisioned.

Additionally, in some embodiments, the NaClO$_2$ based mouth rinse of the present disclosure can further include EDTA. In some embodiments, the disodium EDTA can be in a range of about 0.001 to 0.300% by total volume of the mouth rinse. In some embodiments, the disodium EDTA can be present in an amount of approximately 0.05% by total volume of the mouth rinse. In some embodiments, the NaClO$_2$ based mouth rinse of the present disclosure can further include at least one of sodium hydroxide or sodium carbonate as optional pH adjusters. In some embodiments, the NaClO$_2$ based mouth rinse of the present disclosure can further include potassium hydroxide. In some embodiments, the potassium hydroxide can be in a range of about 0.0001 to about 1.0000% by total volume of the mouth rinse. In such embodiments, the purified water can be adjusted to compensate for the overall volume.

Table 8, shown below, illustrates an additional embodiment of the present disclosure directed towards a NaClO$_2$ based mouth rinse having an alternative formulation.

TABLE 8

| Ingredient | Amount |
|---|---|
| Purified Water | 99.3344% |
| Sodium Chlorite | 0.1600% |
| Sodium Bicarbonate | 0.5000% |
| Citric Acid | 0.0010% |
| Disodium Phosphate | 0.0016% |
| Potassium Hydroxide | 0.0030% |
| Total | 100.00% |
| pH | 9.00 |

In some embodiments, each constituent of the mouth rinse formulation of Table 8 can have varying concentrations. For example, in some embodiments, the purified water can be in a range of about 80.0000 to about 99.9999% by total volume of the mouth rinse. In some embodiments, the sodium chlorite can be in a range of about 0.0500 to about 1.0000% by total volume of the mouth rinse. In some embodiments, the sodium bicarbonate can be in a range of about 0.0500 to about 2.0000% by total volume of the mouth rinse. In some embodiments, the citric acid can be in a range of about 0.0001 to about 1.0000% by total volume of the mouth rinse. In some embodiments, the disodium phosphate can be in a range of about 0.0001 to about 1.0000% by total volume of the mouth rinse. In some embodiments, the potassium hydroxide can be in a range of about 0.0001 to about 1.0000% by total volume of the mouth rinse.

Additionally, in some embodiments, the NaClO$_2$ based mouth rinse of the present disclosure can further include disodium ethylenediaminetetraacetic acid (EDTA). In some embodiments, the disodium EDTA can be in a range of about 0.001 to 0.300% by total volume of the mouth rinse. In some embodiments, the disodium EDTA can be present in an amount of approximately 0.05% by total volume of the mouth rinse. In some embodiments, the NaClO$_2$ based mouth rinse of the present disclosure can further include at least one of sodium hydroxide or sodium carbonate as optional pH adjusters. In such embodiments, the purified water can be adjusted to compensate for the overall volume.

The second mouth rinse, discussed in further detail below, includes the use of xylitol, licorice root extract, and an enzyme (e.g., bromelain) due to the advantageous properties described above. As illustrated above, xylitol has many advantages in oral hygiene, including, but not limited to, anti-adhesion properties, cytotoxic effects and inhibition of mutans streptococci growth, the promotion of salivary flow that can lead to remineralization of teeth, the increase of pH in the oral cavity, and an ability to reduce plaque levels.

In addition to xylitol, the second mouth rinse further includes various licorice extracts. Formulations in a typical embodiment generally include G. glabra and G. uralensis due to their potential in oral hygiene, as discussed above. For example, *G. glabra* is shown to provide a coating effect on teeth, provide for anti-adherent properties against *S. mutans* and *C. albicans*, reduce alveolar bone loss, reduce growth of *C. albicans*, cause a stimulatory effect on bone formation. In addition, *G. uralensis* is shown to inhibit growth and biofilm formation of *P. gingivalis*, inhibit growth of *S. mutans*, provide anti-inflammatory properties, and provide anti-adherent properties against *C. albicans*.

Furthermore, the second mouth rinse further includes an enzyme. In some embodiments, the enzyme is bromelain. Bromelain, as discussed above, provides significant anti-inflammatory properties, thus being useful in eliminating pain caused by mouth sores or irritated soft tissue in, or around, the mouth. The anti-inflammatory benefits of bromelain work synergistically with licorice extracts to provide for fast relief of pain in the oral cavity. This provides the advantage of relieving pain while working in conjunction with xylitol and licorice extract to clean the oral cavity. This proves highly advantageous for patients who suffer from diseases, such as cancer, in which treatment generally causes mouth sores. In some embodiments, the enzyme can include, without limitation, bromelain, actinidin, ficin, papain, and combinations thereof.

Table 9, shown below, illustrates an embodiment of the present disclosure directed toward a xylitol, licorice root extract, and bromelain based mouth rinse.

TABLE 9

| Ingredient | Amount |
| --- | --- |
| Purified Water | 93.2800% |
| Xylitol | 2.0000% |
| Galactoarabinan | 1.5000% |
| Potassium Sorbate | 1.1800% |
| Licorice Root Extract (*G. glabra*) | 0.2100% |
| Licorice Root Extract (*G. uralensis*) | 0.2400% |
| Bromelain | 0.2100% |
| Nisin | 0.2000% |
| Red Root Extract | 0.1800% |
| *Sehinas terebinthifolius* (Brazilian Peppertree) Extract | 0.9000% |
| Potassium Metabisulfite | 0.0600% |
| Citric Acid | 0.0400% |
| Total | 100.0000% |
| pH | 5.8 |

The xylitol, licorice root extract, and bromelain based mouth rinse, as shown in Table 9 above, works by disrupting the energy producing processes of mutans streptococci, reducing adhesion of detrimental and unwanted bacteria, provides anti-inflammatory benefits, and increases salivary flow. As the xylitol, licorice root extract, and bromelain based mouth rinse is not irritating, and even has anti-inflammatory properties, the typical rinsing time is approximately 1 minute. After such rinsing, in a typical embodiment, a user allows the residual to remain for about 30 minutes to 1 hour before eating or drinking. Accordingly, an appropriate time for use could be at night before the user goes to bed. In general, the xylitol, licorice root extract, and bromelain based mouth rinse can have a pH in a range of approximately 5.0 to 6.5. Various formulations, such as the formulation illustrated in Table 9, the xylitol, licorice root extract, and bromelain based mouth rinse can have a pH of approximate 5.8.

The xylitol, licorice root extract, and bromelain based mouth rinse does not have immediate cytotoxic effect on mutans streptococci, as more time is needed for the full benefit of the xylitol, licorice root extract, and bromelain based mouth rinse to take effect. As such, this, in combination with the NaClO$_2$ based mouth rinse, allows for a much longer bacteria and fungi killing time for detrimental bacteria and fungi without irritation. Furthermore, the combination of both the NaClO$_2$ based mouth rinse and xylitol, licorice root extract, and bromelain based mouth rinse provide potential for healing from any inflammation or compromised tissue (e.g. soft tissue irritation or mouth sores). Currently available, and abrasive, mouth rinse products have "quick-kill" abilities. However, unlike the mouth rinses of the present disclosure, the currently available mouth rinses do not have the ability to continue killing and healing that occurs as a result of the xylitol, licorice root extract, and bromelain based mouth rinse, typically used in conjunction with a NaClO$_2$ based mouth rinse as presented herein.

In some embodiments, each constituent of the mouth rinse formulation of Table 9 can have varying concentrations. For example, in some embodiments, the purified water can be in a range of about 85.0000 to about 99.0000% by total volume of the mouth rinse. In some embodiments, the xylitol can be in a range of about 1.0000 to about 5.0000% by total volume of the mouth rinse. In some embodiments, the galactoarabinan can be in a range of about 0.0200 to about 5.0000% by total volume of the mouth rinse. In some embodiments, the potassium sorbate can be in a range of about 0.0200 to about 5.0000% by total volume of the mouth rinse. In some embodiments, the licorice root extract, *G. glabra*, can be in a range of about 0.0500 to about 2.0000% by total volume of the mouth rinse. In some embodiments, the licorice root extract, *G. uralensis*, can be in a range of about 0.0500 to about 2.0000% by total volume of the mouth rinse. In some embodiments, the bromelain can be in a range of about 0.0500 to about 2.0000% by total volume of the mouth rinse.

In some embodiments, the nisin can be in a range of about 0.0500 to about 1.5000% by total volume of the mouth rinse. In some embodiments, the red root extract can be in a range of about 0.0500 to about 1.5000% by total volume of the mouth rinse. In some embodiments, the *S. terebinthifolius* (Brazilian peppertree) extract can be in a range of about 0.0500 to about 2.0000% by total volume of the mouth rinse. In some embodiments, the potassium metabisulfite can be in a range of about 0.0001 to about 1.0000% by total volume of the mouth rinse. In some embodiments, the citric acid can be in a range of about 0.0001 to about 1.0000% by total volume of the mouth rinse. While current formulations utilize bromelain, various other enzymes can be utilized. As such, in some embodiments, the bromelain indicated in the second mouth rinse of the present disclosure can be substituted with another enzyme that can include, without limitation, actinidin, ficin, papain, and combinations thereof.

In addition to xylitol, licorice root extract, and bromelain being combined in a single mouth rinse, in some embodiments of the present disclosure, each of the xylitol, licorice root extract, and bromelain can be independently in a separate mouth rinse. For example, in some embodiments, the second mouth rinse includes only xylitol, and in some embodiments, the second mouth rinse includes only licorice root extract. Further, in some embodiments, the second mouth rinse includes only bromelain. In this manner, each of the xylitol, licorice root extract, and bromelain properties can be utilized separately, that is, not combined in a single formulation. However, in some embodiments, it is desirable to have xylitol, licorice root extract, and bromelain in the second mouth rinse, and as such, in these embodiments, the second mouth rinse includes xylitol, licorice root extract, and bromelain.

In some embodiments, various compounds or compositions that further cause irritation to the oral cavity can be specifically excluded from the mouth rinses of the present disclose. For example, the $NaClO_2$ or the xylitol, licorice root extract, and bromelain mouth rinses of the present disclosure can exclude, for example, extra components that act as irritants or abrasives. In some embodiments, these irritants or abrasives can include, without limitation, alcohol (e.g., methanol, ethanol, or isopropyl alcohol), menthol, cetylpyridinium chloride, hydrogen peroxide, and combinations thereof.

Table 10, shown below, summarizes user feedback in response to nine questions (Q1 to Q9) asked pertaining to the oral rinse compositions of the present disclosure.

TABLE 10

| Answer Choices | Responses | |
|---|---|---|
| Q1. What length of time you have used the mouth rinse system? | | |
| <1 Week | 25.00% | 3 |
| 1-4 Weeks | 41.67% | 5 |
| 5-8 Weeks | 8.33% | 1 |
| 9-12 Weeks | 0.00% | 0 |
| 13-16 Weeks | 0.00% | 0 |
| 16+ Weeks | 25.00% | 3 |
| Q2. What are the reasons you are using the mouth rinse system (check all that apply)? | | |
| Bad Breath | 8.33% | 1 |
| Dry Mouth | 50.00% | 6 |
| Healing Mouth Sores | 50.00% | 6 |
| Periodontal Concerns (i.e., Bleeding Tissue) | 8.33% | 1 |
| Prevention of Reoccurring Episodes | 25.00% | 3 |
| Reducing or Eliminating Mouth Pain | 50.00% | 6 |
| Other | | 3 |
| Q3. What was the initial cause of mouth sores and/or pain (check all that apply)? | | |
| Abrasion from Braces | 0.00% | 0 |
| Allergic Reaction | 0.00% | 0 |
| Cancer/Oncology Treatment | 42.86% | 3 |
| Candidiasis | 14.29% | 1 |
| Canker Sores | 0.00% | 0 |
| Chemical or Thermal Burn | 0.00% | 0 |
| Leukoplakia | 0.00% | 0 |
| Lichen Planus | 0.00% | 0 |
| Lupus | 14.29% | 1 |
| Medications | 14.29% | 1 |
| Periodontal Disease | 0.00% | 0 |
| Rheumatoid Arthritis | 0.00% | 0 |
| Sjogren Syndrome | 28.57% | 2 |
| Slough | 0.00% | 0 |
| Surgical/Trauma | 0.00% | 0 |
| Tooth Extraction | 0.00% | 0 |
| Other | | 6 |
| Q4. Does the mouth rinse system relieve your pain? | | |
| Yes | 75.00% | 9 |
| No | 0.00% | 0 |
| Not Applicable | 25.00% | 3 |
| Q5. On a scale of 1-5, what score best describes how the mouth rinse system provides pain relief for you? | | |
| 1 (Least Pain Relief) | 8.33% | 1 |
| 2 | 8.33% | 1 |
| 3 | 16.67% | 2 |
| 4 | 16.67% | 2 |
| 5 (Most Pain Relief) | 41.67% | 5 |
| Not Applicable | 8.33% | 1 |
| Q6. Has the mouth rinse system addressed your chief concern? | | |
| Yes | 91.67% | 11 |
| No | 8.33% | 1 |

TABLE 10-continued

| Answer Choices | Responses | |
|---|---|---|
| Q7. Please indicate how well the mouth rinse system is helping your condition. | | |
| Healed/Resolved | 33.33% | 4 |
| Improving | 66.67% | 8 |
| No Change | 0.00% | 0 |
| Worsening | 0.00% | 0 |
| Not Applicable | 0.00% | 0 |
| Q8. Is the mouth rinse system easy to use? | | |
| Yes | 100.00% | 12 |
| No | 0.00% | 0 |
| Q9. How likely are you to continue using the mouth rinse system? | | |
| Definitely Would | 72.73% | 8 |
| Probably Would | 18.18% | 2 |
| Probably Would Not | 9.09% | 1 |
| Definitely Would Not | 0.00% | 0 |

In view of the aforementioned, in some embodiments, the present disclosure pertains to a two-part oral rinse composition having a first rinse portion and a second rinse portion. In some embodiments, the first rinse portion includes sodium chlorite ($NaClO_2$) in a first solution and the second rinse portion includes at least one of a sugar alcohol, a licorice root extract, or an enzyme in a second solution.

In some embodiments, the enzyme can include, without limitation, bromelain, actinidin, ficin, papain, and combinations thereof. In some embodiments, the second solution includes the sugar alcohol, the licorice root extract, and the enzyme. In some embodiments, the sugar alcohol is xylitol, the licorice root extract is *Glycyrrhiza glabra* and *Glycyrrhiza uralensis*, and the enzyme is bromelain.

In some embodiments, the first solution has a pH in a range of approximately 8.0 to approximately 12 and the second solution has a pH in a range of approximately 5.0 to approximately 6.5. In some embodiments, the first solution pH is approximately 9 and the second solution pH is approximately 5.8.

In some embodiments, the $NaClO_2$ is present in a range of approximately 0.0500 to approximately 1.0000% by volume of the first solution. In some embodiments, the $NaClO_2$ is present in an amount of approximately 0.1600% by volume of the first solution. In some embodiments, the $NaClO_2$ is present in an amount of approximately 0.1950% by volume of the first solution. In some embodiments, the $NaClO_2$ is present in an amount of approximately 0.1700% by volume of the first solution.

In some embodiments, the first rinse portion further includes a buffering agent that can include, without limitation, sodium hydroxide, calcium hydroxide, potassium hydroxide, borate-type buffering agents, N-cyclohexyl-2-aminoethanesulfonic acid (CHES), monosodium phosphate, calcium carbonate, sodium bicarbonate, disodium phosphate, bicarbonate buffering systems, phosphate buffering systems, alkaline buffering systems, acetate buffering systems, citric acid, and combinations thereof.

In some embodiments, the first rinse portion further includes disodium ethylenediaminetetraacetic acid (EDTA). In some embodiments, the disodium EDTA a range of approximately 0.0010 to approximately 0.3000% by total volume of the first solution. In some embodiments, the disodium EDTA is present in an amount of approximately 0.0500% by total volume of the first solution. In some embodiments, the first rinse portion further includes at least one of sodium hydroxide or sodium carbonate as optional pH adjusters.

In some embodiments, the first rinse portion further includes sodium bicarbonate, citric acid, and disodium phosphate. In some embodiments, the sodium bicarbonate is present in a range of approximately 0.0500 to approximately 2.0000% by volume of the first solution. In some embodiments, the sodium bicarbonate is present in an amount of approximately 0.5000% by volume of the first solution. In some embodiments, the citric acid is present in a range of approximately 0.0001 to approximately 1.0000% by volume of the first solution. In some embodiments, the citric acid is present in an amount of approximately 0.0010% by volume of the first solution. In some embodiments, the disodium phosphate is present in a range of approximately 0.0001 to approximately 1.0000% by volume of the first solution. In some embodiments, the disodium phosphate is present in an amount of approximately 0.0015% by volume of the first solution. In some embodiments, the disodium phosphate is present in an amount of approximately 0.0016% by volume of the first solution.

In some embodiments, the first rinse portion further includes potassium hydroxide. In some embodiments, the potassium hydroxide is present in a range approximately 0.0001 to approximately 1.0000% by volume of the first solution. In some embodiments, the potassium hydroxide is present in an amount of approximately 0.0030% by volume of the first solution.

In some embodiments, the first rinse portion further includes purified water. In some embodiments, the purified water is present in a range approximately 80.0000 to approximately 99.9999% by volume of the first solution.

In some embodiments, the licorice root extract can include, without limitation, *Glycyrrhiza glabra, Glycyrrhiza inflata, Glycyrrhiza uralensis*, and combinations thereof. In some embodiments, the licorice root extract is *Glycyrrhiza glabra* and *Glycyrrhiza uralensis*. In some embodiments, the *Glycyrrhiza glabra* is present in a range of approximately 0.0500 to approximately 2.0000% by volume of the second solution. In some embodiments, the *Glycyrrhiza glabra* is present in an amount of approximately 0.2100% by volume of the second solution. In some embodiments, the *Glycyrrhiza uralensis* is present in a range of approximately 0.0500 to approximately 2.0000% by volume of the second solution. In some embodiments, the *Glycyrrhiza uralensis* is present in an amount of approximately 0.2400% by volume of the second solution.

In some embodiments, the sugar alcohol can include, without limitation, xylitol, sorbitol, and combinations thereof. In some embodiments, the sugar alcohol is xylitol. In some embodiments, the xylitol is present in a range of approximately 1.0000 to approximately 5.0000% by volume of the second solution. In some embodiments, the xylitol is present in an amount of approximately 2.0000% by volume of the second solution.

In some embodiments, the enzyme is bromelain. In some embodiments, the bromelain is present in an amount of approximately 0.0500 to approximately 2.0000% by volume of the second solution. In some embodiments, the bromelain is present in an amount of approximately 0.2100% by volume of the second solution.

In some embodiments, the second rinse portion further includes at least one of galactoarabinan, potassium sorbate, nisin, red root extract, *Schinus terebinthifolius* (Brazilian peppertree) extract, potassium metabisulfite, citric acid, pH buffers, or combinations thereof. In some embodiments, the second rinse portion further includes galactoarabinan, potassium sorbate, nisin, red root extract, *S. terebinthifolius* (Brazilian peppertree) extract, potassium metabisulfite, and citric acid.

In some embodiments, the galactoarabinan is present in a range of approximately 0.0200 to approximately 5.0000% by volume of the second solution. In some embodiments, the galactoarabinan is present in an amount of approximately 1.5000% by volume of the second solution. In some embodiments, the potassium sorbate is present in a range of approximately 0.0200% to approximately 5.0000% by volume of the second solution. In some embodiments, the potassium sorbate is present in an amount of approximately 1.1800% by volume of the second solution. In some embodiments, the nisin is present in a range of approximately 0.0500 to approximately 1.5000% by volume of the second solution. In some embodiments, the nisin is present in an amount of approximately 0.2000% by volume of the second solution. In some embodiments, the red root extract is present in a range of approximately 0.0500 to approximately 1.5000% by volume of the second solution. In some embodiments, the red root extract is present in an amount of approximately 0.1800% by volume of the second solution. In some embodiments, the *S. terebinthifolius* (Brazilian peppertree) extract is present in a range of approximately 0.0500 to approximately 2.0000% by volume of the second solution. In some embodiments, the *S. terebinthifolius* (Brazilian peppertree) extract is present in an amount of approximately 0.9000% by volume of the second solution. In some embodiments, the potassium metabisulfite is present in a range of approximately 0.0001 to approximately 1.0000% by volume of the second solution. In some embodiments, the potassium metabisulfite is present in an amount of approximately 0.0600% by volume of the second solution. In some embodiments, the citric acid is present in a range of approximately 0.0001 to approximately 1.0000% by volume of the second solution. In some embodiments, the citric acid is present in an amount of approximately 0.0400% by volume of the second solution.

In some embodiments, the second rinse portion further includes purified water. In some embodiments, the purified water is present in a range of approximately 85.0000 to 99.0000% by volume of the second solution. In some embodiments, the first rinse portion is utilized as a first mouth rinse and the second rinse portion is utilized as a second mouth rinse.

In another embodiment, the present disclosure pertains to an oral rinse composition having sodium chlorite ($NaClO_2$). In some embodiments, the solution has a pH is in a range of approximately 8.0 to approximately 12. In some embodiments, the pH is a range of approximately 9.0.

In some embodiments, the $NaClO_2$ is present in a range of approximately 0.0500 to approximately 1.0000% by volume of the oral rinse composition. In some embodiments, the $NaClO_2$ is present in an amount of approximately 0.1600% by volume of the oral rinse composition. In some embodiments, the $NaClO_2$ is present in an amount of approximately 0.1950% by volume of the oral rinse composition. In some embodiments, the $NaClO_2$ is present in an amount of approximately 0.1700% by volume of the oral rinse composition.

In some embodiments, the composition further includes a buffering agent that can include, without limitation, sodium hydroxide, calcium hydroxide, potassium hydroxide, borate-type buffering agents, N-cyclohexyl-2-aminoethanesulfonic acid (CHES), monosodium phosphate, calcium carbonate, sodium bicarbonate, disodium phosphate, bicarbonate buffering systems, phosphate buffering systems, alkaline buffering systems, acetate buffering systems, citric acid, and combinations thereof.

In some embodiments, the composition further includes disodium ethylenediaminetetraacetic acid (EDTA). In some embodiments, the disodium EDTA a range of approximately 0.0010 to approximately 0.3000% by total volume of the oral rinse composition. In some embodiments, the disodium EDTA is present in an amount of approximately 0.0500% by total volume of the oral rinse composition. In some embodiments, the composition further includes at least one of sodium hydroxide or sodium carbonate as optional pH adjusters.

In some embodiments, the composition further includes sodium bicarbonate, citric acid, and disodium phosphate. In some embodiments, the sodium bicarbonate is present in a range of approximately 0.0500 to approximately 2.0000% by volume of the oral rinse composition. In some embodiments, the sodium bicarbonate is present in an amount of approximately 0.5000% by volume of the oral rinse composition. In some embodiments, the citric acid is present in a range of approximately 0.0001 to approximately 1.0000% by volume of the oral rinse composition. In some embodiments, the citric acid is present in an amount of approximately 0.0010% by volume of the oral rinse composition. In some embodiments, the disodium phosphate is present in a range of approximately 0.0001 to approximately 1.0000% by volume of the oral rinse composition. In some embodiments, the disodium phosphate is present in an amount of approximately 0.0015% by volume of the oral rinse composition. In some embodiments, the disodium phosphate is present in an amount of approximately 0.0016% by volume of the oral rinse composition.

In some embodiments, the composition further includes potassium hydroxide. In some embodiments, the potassium hydroxide is present in a range approximately 0.0001 to approximately 1.0000% by volume of the oral rinse composition. In some embodiments, the potassium hydroxide is present in an amount of approximately 0.0030% by volume of the oral rinse composition.

In some embodiments, the composition further includes purified water. In some embodiments, the purified water is present in a range approximately 80.0000 to approximately 99.9999% by volume of the oral rinse composition.

In a further embodiment, the present disclosure pertains to an oral rinse composition having at least one of a sugar alcohol, licorice root extract, or an enzyme. In some embodiments, the enzyme can include, without limitation, bromelain, actinidin, ficin, papain, and combinations thereof. In some embodiments, the oral rinse composition has a pH in a range of approximately 5.0 to approximately 6.5. In some embodiments, the pH is approximately 5.8.

In some embodiments, the oral rinse compositions includes the sugar alcohol, the licorice root extract, the enzyme. In some embodiments, the sugar alcohol is xylitol, the licorice root extract is *Glycyrrhiza glabra* and *Glycyrrhiza uralensis*, and the enzyme is bromelain. In some embodiments, the licorice root extract can include, without limitation, *Glycyrrhiza glabra*, *Glycyrrhiza inflata*, *Glycyrrhiza uralensis*, and combinations thereof. In some embodiments, the licorice root extract is *Glycyrrhiza glabra* and *Glycyrrhiza uralensis*. In some embodiments, the *Glycyrrhiza glabra* is present in a range of approximately 0.0500 to approximately 2.0000% by volume of the oral rinse composition. In some embodiments, the *Glycyrrhiza glabra* is present in an amount of approximately 0.2100% by volume of the oral rinse composition. In some embodiments, the *Glycyrrhiza uralensis* is present in a range of approximately 0.0500 to approximately 2.0000% by volume of the oral rinse composition. In some embodiments, the *Glycyrrhiza uralensis* is present in an amount of approximately 0.2400% by volume of the oral rinse composition.

In some embodiments, the sugar alcohol can include, without limitation, xylitol, sorbitol, and combinations thereof. In some embodiments, the sugar alcohol is xylitol. In some embodiments, the xylitol is present in a range of approximately 1.0000 to approximately 5.0000% by volume of the oral rinse composition. In some embodiments, the xylitol is present in an amount of approximately 2.0000% by volume of the oral rinse composition.

In some embodiments, the enzyme is bromelain. In some embodiments, the bromelain is present in an amount of approximately 0.0500 to approximately 2.0000% by volume of the oral rinse composition. In some embodiments, the bromelain is present in an amount of approximately 0.2100% by volume of the oral rinse composition.

In some embodiments, the composition further includes at least one of galactoarabinan, potassium sorbate, nisin, red root extract, *Schinus terebinthifolius* (Brazilian peppertree) extract, potassium metabisulfite, citric acid, pH buffers, or combinations thereof. In some embodiments, the composition further includes galactoarabinan, potassium sorbate, nisin, red root extract, *S. terebinthifolius* (Brazilian peppertree) extract, potassium metabisulfite, and citric acid. In some embodiments, the galactoarabinan is present in a range of approximately 0.0200 to approximately 5.0000% by volume of the oral rinse composition. In some embodiments, the galactoarabinan is present in an amount of approximately 1.5000% by volume of the oral rinse composition. In some embodiments, the potassium sorbate is present in a range of approximately 0.0200% to approximately 5.0000% by volume of the oral rinse composition. In some embodiments, the potassium sorbate is present in an amount of approximately 1.1800% by volume of the oral rinse composition. In some embodiments, the nisin is present in a range of approximately 0.0500 to approximately 1.5000% by volume of the oral rinse composition. In some embodiments, the nisin is present in an amount of approximately 0.2000% by volume of the oral rinse composition. In some embodiments, the red root extract is present in a range of approximately 0.0500 to approximately 1.5000% by volume of the oral rinse composition. In some embodiments, the red root extract is present in an amount of approximately 0.1800% by volume of the oral rinse composition. In some embodiments, the *S. terebinthifolius* (Brazilian peppertree) extract is present in a range of approximately 0.0500 to approximately 2.0000% by volume of the oral rinse composition. In some embodiments, the *S. terebinthifolius* (Brazilian peppertree) extract is present in an amount of approximately 0.9000% by volume of the oral rinse composition. In some embodiments, the potassium metabisulfite is present in a range of approximately 0.0001 to approximately 1.0000% by volume of the oral rinse composition. In some embodiments, the potassium metabisulfite is present in an amount of approximately 0.0600% by volume of the oral rinse composition.

In some embodiments, the citric acid is present in a range of approximately 0.0001 to approximately 1.0000% by volume of the oral rinse composition. In some embodiments, the citric acid is present in an amount of approximately 0.0400% by volume of the oral rinse composition. In some embodiments, the composition further includes purified water. In some embodiments, the purified water is present in a range of approximately 85.0000 to 99.0000% by volume of the oral rinse composition.

In an additional embodiment, the present disclosure pertains to a method for oral hygiene. In general, the method includes rinsing at least one of a first mouth rinse or a second mouth rinse in an oral cavity of a user. In some embodiments, the first mouth rinse includes sodium chlorite ($NaClO_2$) and the second mouth rinse includes at least one of a sugar alcohol, a licorice root extract, or an enzyme.

In some embodiments, the enzyme can include, without limitation, bromelain, actinidin, ficin, papain, and combinations thereof. In some embodiments, the second mouth rinse includes the sugar alcohol, the licorice root extract, and the enzyme. In some embodiments, the sugar alcohol is xylitol, the licorice root extract is *Glycyrrhiza glabra* and *Glycyrrhiza uralensis*, and the enzyme is bromelain. In some embodiments, the rinsing includes use of the first mouth rinse and subsequently using the second mouth rinse. In some embodiments, the $NaClO_2$ is activated by an increase in acidity in the oral cavity to form chlorine dioxide ($ClO_2$). In some embodiments, an increase in $ClO_2$ is the result of a reaction involving $NaClO_2$ and at least one of saliva, bacteria, fungi, or a harmful organism in the oral cavity.

In some embodiments, the first mouth rinse kills at least one of bacteria, yeast, mold, or viruses. In some embodiments, the first mouth rinse kills or inhibits growth of *S. sobrinus, S. mutans*, and other detrimental organisms. In some embodiments, the first mouth rinse prevents oral conditions that can include, without limitation, dental plaque and dental caries, periodontal disease, lichen planus, leukoplakia, oral candidiasis or oral thrush, dry mouth, chemical or thermal burns, and combinations thereof.

In some embodiments, the second mouth rinse provides for at least one of anti-adhesion properties against *S. mutans* and *Candida* spp., provides cytotoxicity against and inhibits growth of mutans streptococci, increases salivary flow, promotes remineralization of teeth, increases pH in the oral cavity, reduces plaque levels in the oral cavity, reduces inflammation of mouth sores, provides healing of mouth sores, reduces pain associated with mouth sores, reduces pain associated with mouth sores caused be chemotherapy or other cancer treatment, provides for healing of mouth sores caused be chemotherapy or other cancer treatment, or combinations thereof.

In some embodiments, the second mouth rinse provides for at least one of surface coating of teeth in the oral cavity, provides for anti-adherent properties against *S. mutans* or *C. albicans*, reduces alveolar bone loss, reduces growth of *C. albicans*, provides stimulatory effects on bone formation, or combinations thereof. In some embodiments, the second mouth rinse provides for at least one of inhibition of growth and biofilm formation of *P. gingivalis*, inhibition of growth of *S. mutans*, provides for anti-inflammatory properties, provides for anti-adherent properties against *C. albicans*, reduces inflammation of mouth sores, provides healing of mouth sores, reduces pain associated with mouth sores, or combinations thereof.

In some embodiments, the first mouth rinse is rinsed in the oral cavity for 45 seconds. In some embodiments, the second mouth rinse is rinsed in the oral cavity for 1 minute. In some embodiments, after rinsing the second mouth rinse the user refrains from eating or drinking for 30 minutes to 1 hour. In some embodiments, the first mouth rinse and the second mouth rinse provide for a synergistic effect to increase bacterial and fungal killing time. In some embodiments, the first mouth rinse decreases likelihood of irritation caused by the $NaClO_2$. In some embodiments, the first mouth rinse has a pH of in a range of approximately 8.0 to approximately 12 and the second mouth rinse has a pH in a range of approximately 5.0 to approximately 6.5. In some embodiments, the first mouth rinse pH is between approximately 9.0 and the second mouth rinse pH is approximately 5.8.

In some embodiments, the $NaClO_2$ is present in a range of approximately 0.0500 to approximately 1.0000% by volume of the first mouth rinse. In some embodiments, the $NaClO_2$ is present in an amount of approximately 0.1600% by volume of the first mouth rinse. In some embodiments, the $NaClO_2$ is present in an amount of approximately 0.1950% by volume of the first mouth rinse. In some embodiments, the $NaClO_2$ is present in an amount of approximately 0.1700% by volume of the first mouth rinse.

In some embodiments, the first mouth rinse further includes a buffering agent that can include, without limitation, sodium hydroxide, calcium hydroxide, potassium hydroxide, borate-type buffering agents, N-cyclohexyl-2-aminoethanesulfonic acid (CHES), monosodium phosphate, calcium carbonate, sodium bicarbonate, disodium phosphate, bicarbonate buffering systems, phosphate buffering systems, alkaline buffering systems, acetate buffering systems, citric acid, and combinations thereof.

In some embodiments, the first mouth rinse further includes disodium ethylenediaminetetraacetic acid (EDTA). In some embodiments, the disodium EDTA a range of approximately 0.0010 to approximately 0.3000% by total volume of the first solution. In some embodiments, the disodium EDTA is present in an amount of approximately 0.0500% by total volume of the first solution. In some embodiments, the first mouth rinse further includes at least one of sodium hydroxide or sodium carbonate as optional pH adjusters.

In some embodiments, the first mouth rinse further includes sodium bicarbonate, citric acid, and disodium phosphate. In some embodiments, the sodium bicarbonate is present in a range of approximately 0.0500 to approximately 2.0000% by volume of the first mouth rinse. In some embodiments, the sodium bicarbonate is present in an amount of approximately 0.5000% by volume of the first mouth rinse. In some embodiments, the citric acid is present in a range of approximately 0.0001 to approximately 1.0000% by volume of the first mouth rinse. In some embodiments, the citric acid is present in an amount of approximately 0.0010% by volume of the first mouth rinse. In some embodiments, the disodium phosphate is present in a range of approximately 0.0001 to approximately 1.0000% by volume of the first mouth rinse. In some embodiments, the disodium phosphate is present in an amount of approximately 0.0015% by volume of the first mouth rinse. In some embodiments, the disodium phosphate is present in an amount of approximately 0.0016% by volume of the first mouth rinse.

In some embodiments, the first mouth rinse further includes potassium hydroxide. In some embodiments, the potassium hydroxide is present in a range approximately 0.0001 to approximately 1.0000% by volume of the first solution. In some embodiments, the potassium hydroxide is present in an amount of approximately 0.0030% by volume of the first solution.

In some embodiments, the first mouth rinse further includes purified water. In some embodiments, the purified water is present in a range approximately 80.0000 to approximately 99.9999% by volume of the first mouth rinse. In some embodiments, the licorice root extract can include, without limitation, *Glycyrrhiza glabra, Glycyrrhiza inflata, Glycyrrhiza uralensis*, and combinations thereof. In some embodiments, the licorice root extract is *Glycyrrhiza glabra* and *Glycyrrhiza uralensis*. In some embodiments, the *Glycyrrhiza glabra* is present in a range of approximately 0.0500 to approximately 2.0000% by volume of the second mouth rinse. In some embodiments, the *Glycyrrhiza glabra* is present in an amount of approximately 0.2100% by volume of the second mouth rinse. In some embodiments, the *Glycyrrhiza uralensis* is present in a range of approximately 0.0500 to approximately 2.0000% by volume of the second mouth rinse. In some embodiments, the *Glycyrrhiza uralensis* is present in an amount of approximately 0.2400% by volume of the second mouth rinse.

In some embodiments, the sugar alcohol can include, without limitation, xylitol, sorbitol, and combinations thereof. In some embodiments, the sugar alcohol is xylitol. In some embodiments, the xylitol is present in a range of approximately 1.0000 to approximately 5.0000% by volume of the second mouth rinse. In some embodiments, the xylitol is present in an amount of approximately 2.0000% by volume of the second mouth rinse.

In some embodiments, the enzyme is bromelain. In some embodiments, the bromelain is present in a range of approximately 0.0500 to approximately 2.0000% by volume of the second mouth rinse. In some embodiments, the bromelain is present in an amount of approximately 0.2100% by volume of the second mouth rinse. In some embodiments, the second mouth rinse further includes at least one of galactoarabinan, potassium sorbate, nisin, red root extract, *Schinus terebinthifolius* (Brazilian peppertree) extract, potassium metabisulfite, citric acid, pH buffers, or combinations thereof. In some embodiments, the second mouth rinse further includes galactoarabinan, potassium sorbate, nisin, red root extract, *S. terebinthifolius* (Brazilian peppertree) extract, potassium metabisulfite, and citric acid.

In some embodiments, the galactoarabinan is present in a range of approximately 0.0200 to approximately 5.0000% by volume of the second solution. In some embodiments, the galactoarabinan is present in an amount of approximately 1.5000% by volume of the second solution. In some embodiments, the potassium sorbate is present in a range of approximately 0.0200% to approximately 5.0000% by volume of the second mouth rinse. In some embodiments, the potassium sorbate is present in an amount of approximately 1.1800% by volume of the second mouth rinse. In some embodiments, the nisin is present in a range of approximately 0.0500 to approximately 1.5000% by volume of the second solution. In some embodiments, the nisin is present in an amount of approximately 0.2000% by volume of the second solution. In some embodiments, the red root extract is present in a range of approximately 0.0500 to approximately 1.5000% by volume of the second solution. In some embodiments, the red root extract is present in an amount of approximately 0.1800% by volume of the second solution.

In some embodiments, the *S. terebinthifolius* (Brazilian peppertree) extract is present in a range of approximately 0.0500 to approximately 2.0000 by volume of the second solution. In some embodiments, the *S. terebinthifolius* (Brazilian peppertree) extract is present in an amount of approximately 0.9000% by volume of the second solution. In some embodiments, the potassium metabisulfite is present in a range of approximately 0.0001 to approximately 1.0000% by volume of the second solution. In some embodiments, the potassium metabisulfite is present in an amount of approximately 0.0600% by volume of the second solution. In some embodiments, the citric acid is present in in a range of approximately 0.0001 to approximately 1.0000% by volume of the second mouth rinse. In some embodiments, the citric acid is present in an amount of approximately 0.0400% by volume of the second mouth rinse. In some embodiments, the second mouth rinse further includes purified water. In some embodiments, the purified water is present in a range of approximately 85.0000 to 99.0000% by volume of the second mouth rinse.

In a further embodiment, the present disclosure pertains to a two-part oral rinse composition having a first rinse portion including sodium chlorite ($NaClO_2$) in a first solution and a second rinse portion including a sugar alcohol, a licorice root extract, and an enzyme that can include, without limitation, bromelain, actinidin, ficin, papain, and combinations thereof in a second solution. In some embodiments, the first solution has a pH in a range of approximately 8.0 to approximately 12 and the second solution has a pH in a range of approximately 5.0 to approximately 6.5.

In some embodiments, the $NaClO_2$ is present in a range of approximately 0.0500 to approximately 1.0000% by volume of the first solution. In some embodiments, the first rinse portion further includes sodium bicarbonate, citric acid, disodium phosphate, and potassium hydroxide. In some embodiments, the sodium bicarbonate is present in a range of approximately 0.0500 to approximately 2.0000% by volume of the first solution. In some embodiments, the citric acid is present in a range of approximately 0.0001 to approximately 1.0000% by volume of the first solution. In some embodiments, the disodium phosphate is present in a range of approximately 0.0001 to approximately 1.0000% by volume of the first solution. In some embodiments, the potassium hydroxide phosphate is present in a range of approximately 0.0001 to approximately 1.0000% by volume of the first solution.

In some embodiments, the licorice root extract is *Glycyrrhiza glabra* and *Glycyrrhiza uralensis*. In some embodiments, the *Glycyrrhiza glabra* is present in a range of approximately 0.0500 to approximately 2.0000% by volume of the second solution. In some embodiments, the *Glycyrrhiza uralensis* is present in a range of approximately 0.0500 to approximately 2.0000% by volume of the second solution. In some embodiments, the sugar alcohol is xylitol and is present in a range of approximately 1.0000 to approximately 5.0000% by volume of the second solution. In some embodiments, the enzyme is bromelain and is present in an amount of approximately 0.0500 to approximately 2.0000% by volume of the second solution.

In some embodiments, the second rinse portion further includes galactoarabinan, potassium sorbate, nisin, red root extract, *S. terebinthifolium* (Brazilian peppertree) extract, potassium metabisulfite, and citric acid. In some embodiments, the galactoarabinan is present in a range of approximately 0.0200 to approximately 5.0000% by volume of the second solution. In some embodiments, the potassium sorbate is present in a range of approximately 0.0200% to approximately 5.0000% by volume of the second solution. In some embodiments, the nisin is present in a range of approximately 0.0500 to approximately 1.5000% by volume of the second solution. In some embodiments, the red root extract is present in a range of approximately 0.0500 to approximately 1.5000% by volume of the second solution. In some embodiments, the *S. terebinthifolium* (Brazilian peppertree) extract is present in a range of approximately 0.0500 to approximately 2.0000% by volume of the second solution. In some embodiments, the potassium metabisulfite is present in a range of approximately 0.0001 to approximately 1.0000% by volume of the second solution. In some embodiments, the citric acid is present in a range of approximately 0.0001 to approximately 1.0000% by volume of the second solution.

Although various embodiments of the present disclosure have been described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A two-part oral rinse composition comprising:
    a first rinse portion comprising sodium chlorite in a first solution; and
    a second rinse portion comprising a sugar alcohol, a licorice root extract, and an enzyme selected from the group consisting of bromelain, actinidin, ficin, papain, and combinations thereof in a second solution; and
    wherein the first solution has a pH in a range of 8.0 to 12 and the second solution has a pH in a range of 5.0 to 6.5.

2. The two-part oral rinse composition of claim 1, wherein the sodium chlorite is present in a range of 0.0500 to 1.0000% by volume of the first solution.

3. The two-part oral rinse composition of claim 1, the first rinse portion further comprising sodium bicarbonate, citric acid, disodium phosphate, and potassium hydroxide.

4. The two-part oral rinse composition of claim 3, wherein the sodium bicarbonate is present in a range of 0.0500 to 2.0000% by volume of the first solution.

5. The two-part oral rinse composition of claim 3, wherein the citric acid is present in a range of 0.0001 to 1.0000% by volume of the first solution.

6. The two-part oral rinse composition of claim 3, wherein the disodium phosphate is present in a range of 0.0001 to 1.0000% by volume of the first solution.

7. The two-part oral rinse composition of claim 3, wherein the potassium hydroxide phosphate is present in a range of 0.0001 to 1.0000% by volume of the first solution.

8. The two-part oral rinse composition of claim 1, wherein the licorice root extract is *Glycyrrhiza glabra* and *Glycyrrhiza uralensis*.

9. The two-part oral rinse composition of claim 8, wherein the *Glycyrrhiza glabra* is present in a range of 0.0500 to 2.0000% by volume of the second solution.

10. The two-part oral rinse composition of claim 8, wherein the *Glycyrrhiza uralensis* is present in a range of 0.0500 to 2.0000% by volume of the second solution.

11. The two-part oral rinse composition of claim 1, wherein the sugar alcohol is xylitol, and wherein the xylitol is present in a range of 1.0000 to 5.0000% by volume of the second solution.

12. The two-part oral rinse composition of claim 1, wherein the enzyme is bromelain, and wherein the bromelain is present in an amount of 0.0500 to 2.0000% by volume of the second solution.

13. The two-part oral rinse composition of claim 1, the second rinse portion further comprising galactoarabinan, potassium sorbate, nisin, red root extract, *S. terebinthifolium* extract, potassium metabisulfite, and citric acid.

14. The two-part oral rinse composition of claim 13, wherein the galactoarabinan is present in a range of 0.0200 to 5.0000% by volume of the second solution.

15. The two-part oral rinse composition of claim 13, wherein the potassium sorbate is present in a range of 0.0200% to 5.0000% by volume of the second solution.

16. The two-part oral rinse composition of claim 13, wherein the nisin is present in a range of 0.0500 to 1.5000% by volume of the second solution.

17. The two-part oral rinse composition of claim 13, wherein the red root extract is present in a range of 0.0500 to 1.5000% by volume of the second solution.

18. The two-part oral rinse composition of claim 13, wherein the *S. terebinthifolium* extract is present in a range of 0.0500 to 2.0000% by volume of the second solution.

19. The two-part oral rinse composition of claim 13, wherein the potassium metabisulfite is present in a range of 0.0001 to 1.0000% by volume of the second solution.

20. The two-part oral rinse composition of claim 13, wherein the citric acid is present in a range of 0.0001 to 1.0000% by volume of the second solution.

* * * * *